(12) United States Patent
Tran et al.

(10) Patent No.: US 6,524,299 B1
(45) Date of Patent: Feb. 25, 2003

(54) FLOW-DIRECTED CATHETER

(75) Inventors: Quang Q. Tran, Fremont, CA (US); Marlowe Patterson, Milpitas, CA (US); Henry Nita, Milpitas, CA (US); Paul C. Slaikeu, Hayward, CA (US)

(73) Assignee: Target Therapeutics, Inc., Fremont, CA (US)

( * ) Notice: Subject to any disclaimer, the term of this patent is extended or adjusted under 35 U.S.C. 154(b) by 782 days.

(21) Appl. No.: 08/838,685

(22) Filed: Apr. 9, 1997

(51) Int. Cl.[7] .............................................. A61M 25/00
(52) U.S. Cl. ...................................................... 604/523
(58) Field of Search ................................ 604/280–282, 604/264, 523, 524, 525, 528

(56) References Cited

U.S. PATENT DOCUMENTS

| | | |
|---|---|---|
| 3,566,874 A | 3/1971 | Shepherd et al. |
| 3,608,555 A | 9/1971 | Greyson |
| 4,282,876 A | 8/1981 | Flynn |
| 4,430,083 A | 2/1984 | Ganz et al. |
| 4,495,134 A | 1/1985 | Ouchi et al. |
| 4,636,346 A | 1/1987 | Gold et al. |
| 4,690,175 A | 9/1987 | Ouchi et al. |
| 4,884,579 A | 12/1989 | Engelson |
| 4,899,787 A | 2/1990 | Ouchi et al. |
| 5,045,072 A | 9/1991 | Castillo et al. |
| 5,171,232 A | 12/1992 | Castillo et al. |
| 5,234,416 A | 8/1993 | Macaulay et al. |
| 5,300,048 A | 4/1994 | Drewes, Jr. et al. |
| 5,308,342 A | 5/1994 | Sepetka et al. |
| 5,336,205 A | 8/1994 | Zenzen et al. |
| 5,533,985 A | 7/1996 | Wang |
| 5,538,512 A | 7/1996 | Zenzen et al. |
| 5,584,821 A | 12/1996 | Hobbs et al. |

FOREIGN PATENT DOCUMENTS

EP 0 528 181 A1 2/1993

Primary Examiner—Brian L. Casler

(57) ABSTRACT

This invention is to a minimally invasive surgical device. In particular, the invention relates to an infusion catheter which may be used in cardiovascular and endovascular procedures to deliver diagnostic, therapeutic, or vasoocclusive agents to a target site accessible through the vasculature. The device is a flow-directed infusion catheter having a variety of sections of different flexibilities with tapered junctions between those sections. The inventive catheter is directed to that target site by a flow of blood to the site.

9 Claims, 2 Drawing Sheets

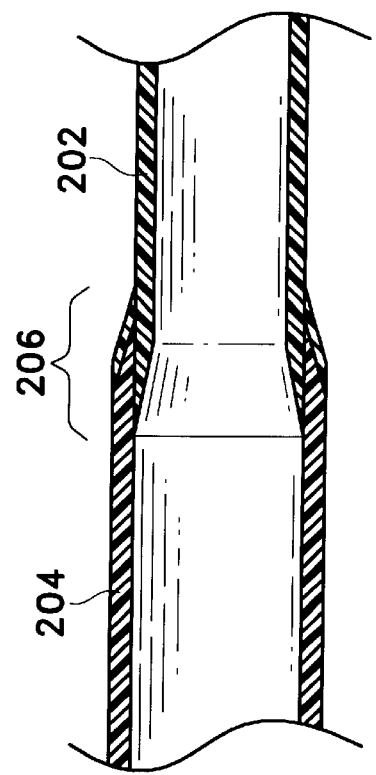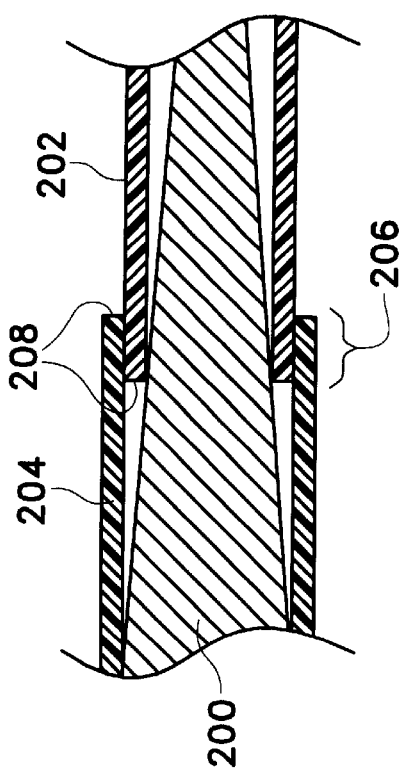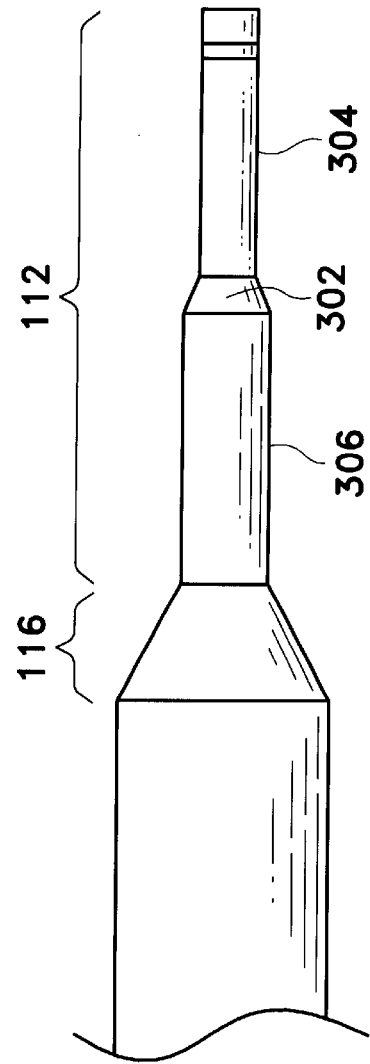
Fig. 2B
Fig. 2A
Fig. 3

FLOW-DIRECTED CATHETER

FIELD OF THE INVENTION

This invention is to a minimally invasive surgical device. In particular, the invention relates to an infusion catheter which may be used in cardiovascular and endovascular procedures to deliver diagnostic, therapeutic, or vasoocclusive agents to a target site accessible through the vasculature. The device is a flow-directed infusion catheter having a variety of sections of different flexibilities with tapered junctions between those sections. The inventive catheter is directed to that target site by a flow of blood to the site.

BACKGROUND OF THE INVENTION

As the cost of classical surgery increases and the sophistication of minimally invasive surgical technology improves, the use of catheters as means for delivering diagnostic and therapeutic agents to internal target sites has similarly increased. Of particular interest herein are catheters which may be used to access target sites through the circulatory system.

There are a number of generalized procedures for placing catheters within vessels in the body for accessing sites that are difficult to approach. Specifically, one such technique involves the use of a torqueable guidewire which is alternately rotated and advanced to the target site. As the guidewire is advanced, the catheter is then advanced along the wire until the distal end of the catheter is positioned at the desired target site. An early example of this technique is described in U.S. Pat. No. 4,884,579, to Engelson. Although the technology involved in such a catheter is quite sophisticated, many consider the catheter to be a second choice when a highly time-sensitive situation is to be treated. This is due to the comparatively time-consuming nature of rotating and advancing the guidewire and then advancing the catheter over the guidewire through the vasculature.

Another technique for advancing a catheter to a target site is to employ a highly flexible catheter having an inflatable, but pre-punctured, balloon at its distal end. In use, the balloon is partially inflated, and carried by blood flow to the target site. During such a placement procedure, the balloon is continually inflated to replenish fluid leaking from the balloon. This technique, too, has major drawbacks, including the fact that the catheter material is so flexible that the catheter cannot be pushed from the proximal end without buckling some portion of the catheter. Instead, the catheter must be advanced using injected fluid to inflate the balloon in order to propel the catheter to the target site. There is always the risk of rupture of a vessel by a balloon that has been too highly inflated.

Flow-directed catheters have also been proposed which do not use such leaking balloon technology. Specifically, the catheters are so flexible at their distal and mid regions that they are able to be carried by blood flowing to a target site. Examples of such products are described in U.S. Pat. No. 5,336,205 (to Zenzen et al.) and U.S. Pat. No. 5,538,512 (to Zenzen et al.). These catheters have in common the presence of a relatively stiff tapered proximal segment, a relatively flexible and strong distal segment, and a transition section between those proximal and distal segments which is intermediate in flexibility. The distal segment has a burst pressure release of 195 psi and is made of a material that shows exceptional deflection when a minor force is placed upon such distal portion.

Neither of these patented devices have the structure of the device described below.

SUMMARY OF THE INVENTION

This invention is an infusion catheter for placement within the vasculature. In particular, it may be delivered to a target site by means of blood flow to that site. It may be used to deliver diagnostics, therapeutics, or vasoocclusive agents via tortuous, small vessel pathways to the selected site. The infusion catheter has an elongate tubular body having proximal and distal ends and a lumen extending between those ends.

The elongate tubular body is formed of a comparatively stiff proximal segment, a comparatively flexible and fairly strong distal segment, and a transition section between the proximal and distal segments that is intermediate in its flexibility. It may have more segments if such is desired. In general, the proximal segment is of a specific diameter, the midsection is of a smaller constant diameter, and the most distal segment may be of a relatively constant and comparatively smallest diameter. The devices typically have a tapered joint placed between each of the noted segments. Highly preferred is a structure which has been annealed so that the thermoplastics found at the various joints have been smoothed and the crystallinity of the polymers in the various catheter segments has been lessened.

The materials preferably making up the various catheter segments are desirably thermoplastics, particularly polyvinylchloride (PVC) or polyurethane. Also desirably, the polymers may contain a radio-opacifier such as bismuth subcarbonate. Each of the segments may contain this radio-opacifier additive but is especially preferred that it be placed in the distal and middle segments. Finally, it is highly desirable that the catheter assembly be of such flexibility that it be combined with a stylet for delivery in a guiding catheter to a region of the body through a larger guiding catheter. Once the distal end of the inventive catheter is near the distal end of the guide catheter, the stylet is removed and only then is the blood flow used to extend the inventive catheter to its target site.

The interior and exterior of the device may be coated with a hydrophilic coating.

BRIEF DESCRIPTION OF THE DRAWINGS

FIG. 2A shows, in cross-section, a junction of the inventive catheter during its assembly using a tapered mandrel.

FIG. 2B shows the catheter joint of FIG. 2A after the assembly step is completed.

FIG. 3 shows a side view of an alternative distal section of the inventive catheter having an additional in-section step.

DESCRIPTION OF THE INVENTION

Figure 1:
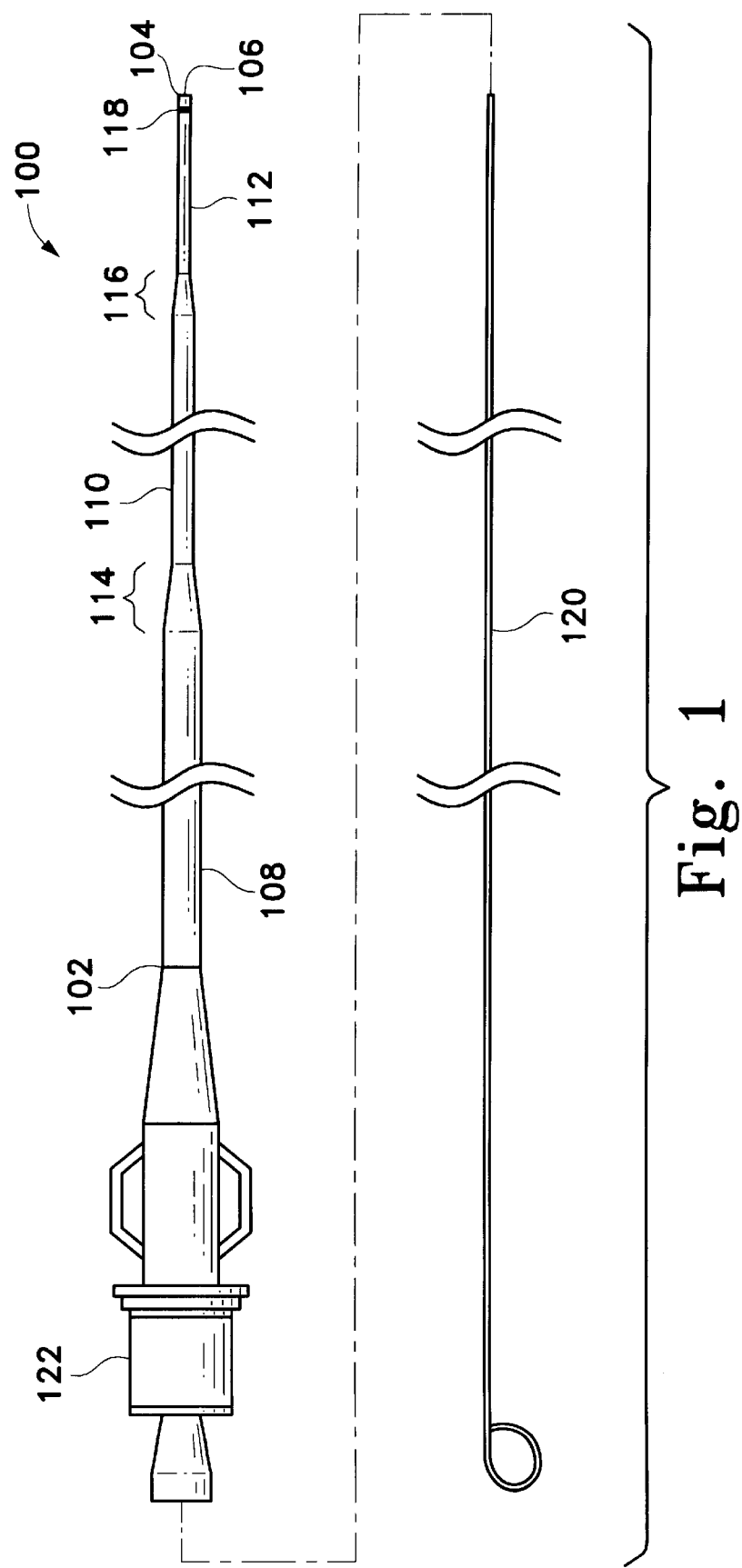
FIG. 1 shows, in side-view, a flow-directed catheter made according to the preferred embodiment of the invention.

FIG. 1 shows a flow-directed infusion catheter (100) made according to a preferred embodiment of the invention. The catheter (100) has an elongate tubular body with a proximal end (102) and a distal end (104) and an inner lumen (106) extending between those ends. For this variation of the inventive catheter (100), the tubular body has three segments; a comparatively stiff proximal segment (108), a comparatively more flexible intermediate section (110), and a most flexible distal segment (112). Between the proximal segment (108) and the mid segment (110) lies a tapering joint (114). Similarly, between middle segment (110) and distal segment (112) lies a tapering joint (116). The flexible distal segment (112) may have one or more radiopaque bands (118) allowing clear visualization of the distal tip using fluoroscopy.

The flexible distal segment (112) has an open end which allows for the infusion of diagnostic, therapeutic, or vasoocclusive agents into the target site. The flexible distal segment (112) may be made of a polymer which is inherently quite springy and flexible and biologically compatible such as polyvinylchloride (PVC), polyurethane, silicones, or various block copolymers of polyamides with these polymers or blends or alloys of them. This segment may be doped with radio-opaque materials such as barium sulfate, bismuth trioxide, bismuth subcarbonate, powdered tungsten, powdered tantalum, or the like. Preferred is bismuth subcarbonate. It is typical that contents of this section may include between 10% and 30% by weight of the radiopaque material, preferably 20–25%. The preferred polymers are polyurethane and PVC. Most preferred is PVC. The range of hardness for the materials of this section are Shore 55A to 75A, preferably 60A to 70A, and most preferably in the neighborhood of Shore 65A.

The distal segment (112) typically makes up between 5% and 25% of the total length of the tubular member and is generally between 5 and 40 cm. in length. Most preferably, it is between 10–30 cm. in length. The outer diameter of distal segment (112) is preferably between 1 F and 2.5 F. Most preferably is an outer diameter in the neighborhood of 1.6 F and 2 F, most preferred is 1.8 F. It should be noted that this is an extremely small catheter diameter.

Middle segment (110) may be made of the same general materials as is the distal segment. Of course, the flexibility of the material making up the middle segment is preferably moderately more stiff than is the distal section. This is to say that the flexural modulus of the plastic making up the section is between Shore 65A and 85A, preferably 67A and 77A, and most preferably about 72A. The length of midsection (110) is typically between 10–20% of the overall length of the tubular member. The physical length is typically between 20–40 cm. and preferably between 20—30 cm. The outer diameter of middle section (110) desirably is between 2 F and 3 F, preferably between 2.2 F and 2.6 F.

Proximal segment (108) similarly may be made of a polymeric material such as those discussed above with regard to the other two segments. However, since it is relatively more stiff than the other two sections, it may also be produced of a material such as a polyamides (Nylon) and polyethylene, e.g. high density, or polypropylene. Preferably, on the basis of compatibility with the preferred polymers in the other segments, the proximal segment is PVC or polyurethane, preferably PVC. The proximal segment (108) may also comprise a braided shaft (a polymer outer core with a metallic mesh inner core) or a coil (a helically wound wire or ribbon on a polymer core further covered by a polymer outer cover). The proximal segment typically makes up between 60–80% of the total length of the tubular member and is typically between 100–140 cm. in length, preferably 105–120 cm. in length. The outer diameter is larger than that of the middle section (110) and typically is between 2.9 F and 3.5 F, preferably 2.7 F to 3.2 F, and most preferably 3 F. The wall thickness is preferably between about 4 mils and 12 mils.

The polymers used in proximal section (108) typically are blended to include some amount of one or more of the radiopaque powdered materials discussed above.

Highly preferred in this variation of the invention is the use of a distal section (112), midsection (110), and proximal section (108) which are of a substantially constant diameter and in which the joints (114) and (116) are tapered. Use of tapered joints (114) and (116) provide for ease of assembly and allow for a smooth transition between the segments.

A long stylet (120) is also shown. The stylet is shorter than the overall length of the catheter assembly (100) and unlike a guidewire does not precede the catheter through the vasculature, both because of its short length and absence of a taper or shapeable tip. Stylet (120) is placed interior to the catheter assembly (100) during the time it is initially into the body. That is to say that the stylet provides sufficient stiffness to allow to be manipulated through a guiding catheter assembly to a region near the target site in the vasculature.

The most proximal portion of the catheter includes the typical means (122) for joining the proximal end of the catheter to other devices using, e.g., helically cut threads or the like.

FIG. 2A shows one step in producing joints (114) and (116). FIG. 2A shows a tapered mandrel (200) which typically would be made of a metal such as stainless steel or other heat-resistant material. A smaller diameter polymeric tubing (202) and a larger diameter polymeric tubing (204) are shown placed therein. The overlap (206) between larger polymeric tubing (204) and smaller polymeric tubing (202) is shown therein. Overlap (206) may be of any convenient length but we have found that for a catheter of this type, an overlap of 0.05–3 mm. is desirable. For PVC, an overlap of about 1 mm. is highly desirable. The ends (208) of the respective polymeric tubing (202) and (204) may be chamfered or rounded if so desired.

The tapered mandrel is for the specific purpose of providing shape to the overlap (206) during the step of heating that overlap (206).

FIG. 2B shows the overall shape of the overlap joint (206) as was shown prior to heating in FIG. 2A. A larger diameter (204) may be proximal section (108) where smaller diameter tubing (202) is midsection (110). Similarly, large diameter tubing (204) may be middle segment (110) where smaller diameter tubing (202) is distal segment (112). Overlap (206) may be either joint (114) or joint (116). The inner profile of overlap (206) generally follows that of tapered mandrel (200). The construction of overlap (206) during the heating step must be done with some care. We have found, for instance, that when fusing of a joint between two sections of shore 72A PVC having 23% bismuth carbonate with a section of tubing having a shore hardness of 65A also containing 23% bismuth carbonate is readily formed at a temperature of 375° F. for 10–15 seconds. For harder materials, e.g., a 1 mm. overlap joint of Shore 77D PVC with 16% bismuth carbonate and a smaller tubing of Shore 72A PVC with 23% bismuth carbonate, a heating step of 415° F. for 10–15 seconds is adequate.

FIG. 3 shows a variation of the distal portion (112) of the inventive catheter (100) in which that section (112) is of two different diameters. The section is of the same material however, throughout the section. The length of midsection taper (302) is usually the same as the tapers (114, 116) between sections mentioned above. The diameter of the smaller portion (304) of the distal section (116) is typically about 50% to 75% of the diameter of the larger diameter portion (306) of that section (116). Use of the same polymer in that section (116) provides for excellent softness and suppleness in flowing through arterial vasculature.

We have also found that when using either PVC or a polyurethane, particularly when the PVC's are infused with plasticizers such as epoxidized soybean oil, the catheter assembly is provided with substantial added flexibility and conformability where the catheter (100) is "annealed" after the tapered joints (104) and (106) have been produced.

The exterior and interior surfaces of catheter assembly (100) may be treated with a hydrophilic covering much as recited in the patent to Zenzen et al. (U.S. Pat. No. 5,538,512), the entirety of which is incorporated by reference.

Although preferred embodiments of the invention have been described herein, it will be recognized that a variety of changes and modifications.

We claim as our invention:

1. A blood-flow directable catheter constructed of materials and having size and flexibility such that said blood-flow directable is directable to a target site within the vasculature of the human body by blood flow within that vasculature which blood-flow directable catheter comprises an elongate tubular member having a proximal end and a distal end, a length between said proximal end and a distal end, said elongate tubular member comprising:
   a.) a distal segment made of a thermoplastic polymer having a modulus of elasticity which renders said distal segment relatively more flexible than both an intermediate segment and a proximal segment,
   b.) an intermediate segment made of a thermoplastic polymer having a modulus of elasticity which renders said intermediate segment relatively more flexible than said proximal segment and less flexible than said distal segment and wherein said intermediate segment has a relatively constant diameter,
   c.) a proximal segment comprising a thermoplastic polymer having a modulus of elasticity which renders said proximal segment relatively less flexible than said intermediate segment and said distal segment and wherein said proximal segment has a relatively constant diameter,
   d.) a tapered joint joining said intermediate segment and said proximal segment, and
   e.) a tapered joint joining said intermediate segment and said distal segment.

2. The blood-flow directable catheter of claim 1 wherein said elongate tubular member has been heat treated after assembly.

3. The blood-flow directable catheter of claim 1 wherein said thermoplastic polymer in said intermediate segment and said distal segment contains a radio-opaque filler.

4. The blood-flow directable catheter of claim 3 wherein said thermoplastic polymer in said proximal segment contains a radio-opaque filler.

5. The blood-flow directable catheter of claim 1 further comprising a stylet having a length no longer than the length between said elongate member proximal end and distal end.

6. The blood-flow directable catheter of claim 1 wherein said thermoplastic polymer in said intermediate segment, said distal segment, and said proximal segment comprises polyvinylchloride.

7. The blood-flow directable catheter of claim 1 wherein said distal segment has a relatively constant diameter.

8. The blood-flow directable catheter of claim 1 wherein said distal segment has two portions of different diameter.

9. The blood-flow directable catheter of claim 1 wherein said tapered joint joining said intermediate segment and said proximal segment and said tapered joint joining said intermediate segment and said distal segment are molded of overlapping portions respectively of said intermediate portions and said proximal segment and said intermediate segment and said distal segment.

\* \* \* \* \*